Figure 1:
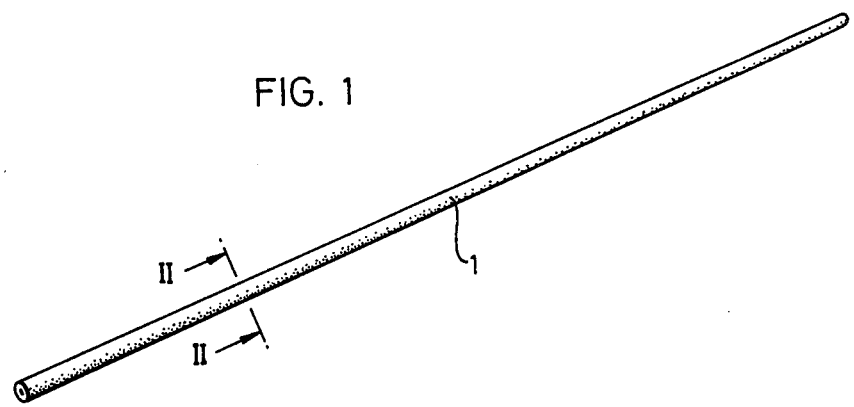

United States Patent [19]

Jones et al.

[11] 4,185,626
[45] Jan. 29, 1980

[54] MATERIAL DETECTABLY BY X-RAYS

[75] Inventors: Graham Jones, Skipton; Geoffrey Unwin, Kelbrook, near Colne, both of England

[73] Assignee: Johnson & Johnson, New Brunswick, N.J.

[21] Appl. No.: 862,479

[22] Filed: Dec. 20, 1977

[51] Int. Cl.² .............................................. A61L 15/00
[52] U.S. Cl. .................................... 128/156; 128/335.5
[58] Field of Search .................. 424/4; 128/335.5, 156

[56] References Cited

U.S. PATENT DOCUMENTS

| 3,194,239 | 7/1965 | Sullivan | 128/335.5 |
| 3,540,452 | 11/1970 | Usher et al. | 128/335.5 |
| 3,847,156 | 11/1974 | Trumble | 128/335.5 |

FOREIGN PATENT DOCUMENTS

| 333980 | 8/1930 | United Kingdom | 424/4 |
| 354284 | of 1931 | United Kingdom | 128/335.5 |
| 393505 | 3/1932 | United Kingdom | 128/335.5 |
| 640541 | 7/1950 | United Kingdom . | |
| 716923 | 10/1954 | United Kingdom . | |
| 790417 | 2/1958 | United Kingdom | 424/4 |
| 795870 | 6/1958 | United Kingdom . | |
| 884143 | 12/1961 | United Kingdom | 424/4 |
| 1253979 | 11/1971 | United Kingdom . | |
| 1257709 | 12/1971 | United Kingdom . | |
| 1336213 | 11/1973 | United Kingdom . | |
| 1336368 | 11/1973 | United Kingdom . | |
| 1372524 | 10/1974 | United Kingdom . | |
| 1391262 | 4/1975 | United Kingdom . | |

Primary Examiner—Robert E. Bagwill
Attorney, Agent, or Firm—Irving Newman

[57] ABSTRACT

X-ray detectable filament of elastomeric material for incorporation in a surgical dressing, including an X-ray opaque substance in sufficient proportions to render the filament detectable by X-rays, the filament incorporating throughout its length a continuous, preferably internal, reinforcing thread such as a textile yarn.

6 Claims, 2 Drawing Figures

U.S. Patent  Jan. 29, 1980  4,185,626

MATERIAL DETECTABLY BY X-RAYS

The present invention relates to an improved filamentary material the presence of which is detectable by means of X-rays.

During surgery every effort is made to ensure that surgical sponges are not left in the body of the patient but it remains desirable to employ sponges containing material detectable by means of X-rays so that a surgeon can determine, by taking X-rays without re-opening the patient, whether or not a sponge has been left in the body and where in the wound an attempt should be made to recover it. In this context surgical sponges include not only gauze swabs but also laparotomy pads and cotton balls.

Material included in a surgical sponge to render it detectable by X-rays must, among other things, be opaque to X-rays, capable of sterilisation, not absorbable in body fluids, of a reasonable cost, visually detectable, firmly anchored to the sponge, free from abrasive and irritant effects, non-fraying and lacking toxic properties. In the case of, for example, reusable laparotomy pads the material should be launderable.

The X-ray detectable material may be provided within the sponge or on its exterior, or be integrated with the sponge material, for instance by weaving, knitting, adhesion, or stitching at intervals, but it must not interfere with the quality of softness of the sponge material.

A suitable X-ray opaque material which is used for the foregoing purpose is a filament or ribbon composed of an elastomer that is loaded with X-ray opaque filler material and is non-tacky at ordinary temperatures. The elastomer may be any natural or synthetic plastics material with flexible or rubber-elastic properties, and a non-toxic plasticiser may be included if necessary. The filament may usefully be given a sinuous configuration for ease of recognition among body organs and tissues under X-ray observation. Such materials are described in our United Kingdom Pat. Nos. 640,541, 716,923 and 795,870. Typical elastomers are polyisobutylene, polyvinyl chloride, and copolymers of vinyl acetate and vinyl chloride.

As X-ray opaque filler material an element such as barium, of atomic weight above 100, or one of its compounds, may be used, as long as they are not toxic. It is particularly advantageous to use barium sulphate. An amount of X-ray opaque filler of the order of 40 to 90 percent by weight, more preferably 60 to 70 percent, based on the weight of the elastomer, is found suitable. A minor amount, e.g., 0.5 percent, based on the weight of the elastomer, of a pigment such as carbon black, is also preferably included in order to render the material visually distinctive.

Extruded filaments containing the abovementioned X-ray opaque filler and a pigment, of a thickness of 17 mils or more, when incorporated in a sponge inadvertently left in a patient, show up on exposure to X-rays as a distinctive shadow or pattern easily discernible and distinguished from surrounding tissues.

In the production and incorporation of such filamentary material, for instance during extrusion and winding onto a core, or in feeding the filament to the machine forming a dressing in which the filament is to be incorporated, the filament is liable to be subjected to tension, or strain during stretching, which may give rise to breaks since the material is heavily loaded with filler and not inherently tough, or to changes in dimensions after incorporation into a surgical sponge, due to relaxation after strain. These undesirable effects reduce the acceptability of the material and may even permit it to disperse from the dressing.

It is an object of the invention to provide an X-ray detectable material of the type described, having improved strength and dimensional stability. The invention is described with reference to its application in surgical dressings but it will be apparent that it can be employed more generally where an X-ray tell-tale is required.

According to the invention an X-ray detectable material suitable for incorporation in a surgical dressing comprises a filament of elastomeric material including an X-ray opaque substance such as a filler in sufficient proportions to render the filament detectable by X-rays, said filament incorporating throughout its length a preferably internal and most preferably central, continuous reinforcing thread.

The elastomeric material and filler may be any of those known for the purpose, such as those described above and exemplified by polyvinyl chloride polymers or copolymers filled with 40 to 90 percent by weight of powdered barium sulphate and preferably pigmented with carbon black.

The reinforcing thread is preferably internal to the filament but it may, for instance be externally incorporated, for example by spiral winding and adhesive bonding. The reinforcing thread, which need not be chemically or physically related to the elastomer in any special way except of course as to length and diameter, can in principle be a metal strand, say of copper or steel, in which case the reinforcement lends X-ray opacity, but in view of the properties to be fulfilled by the filamentary material it is preferred to employ as reinforcing thread a continuous textile yarn, for instance of fine cotton. The use of monofilament, multifilament or bulked polyester or polyamide fibre is also contemplated. Optimum yarn strength in relation to yarn thickness provides for maximum economy in filled elastomeric material.

The reinforced filament may be readily produced by extrusion on the type of equipment used for making insulated electric wire, employing for instance a crosshead extrusion die. The desired thickness of the resultant filament depends primarily on the need for sufficient opacity to X-rays, and therefore upon the particular filler included. In the case of barium sulphate in our preferred elastomer, it is found that a transverse path length through filled elastomer of about 28 mils is adequate. Adequate reinforcement is generally obtainable with a thread yarn of 30's Tex or less. A resultant filament thickness of at least about 35 mils is accordingly desirable to take into account the reinforcement, and is also suitable from the viewpoints of strength and ease of incorporation into other materials. The filament can, however, be larger or smaller in cross-section in particular cases subject to considerations of strength or economy. The elastomer preferably is, but need not be, rendered adherent to the reinforcing thread.

Reinforcing threads of various deniers and of other forms may be used as long as they do not significantly alter the flexibility and other properties required in the product. Metal may for instance be incorporated in the reinforcement by using a metallised textile yarn as the reinforcing thread.

During the production and incorporation of the filamentary material into other goods, and subsequently, the reinforcement serves to restrain the filament from undue dimensional change or actual breakage leading to escape of the X-ray detectable member from the goods.

The reinforced filament may be attached to a surgical sponge, for instance of gauze, by heat sealing the elastomeric material of the filament to the gauze by the application of heat and pressure.

Figure 2:
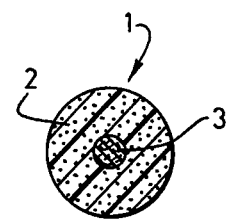

The invention is further illustrated in the accompanying drawings in which:

FIG. 1 is a perspective view of a length of reinforced elastomeric thread of the invention; and FIG. 2 is a cross-section on the line II—II of FIG. 1.

Referring to the Figures, a filament 1 of filled elastomeric material 2 in which the filler is an X-ray opaque material, is shown having an internal and centrally disposed reinforcing yarn 3 incorporated in the filament by extrusion.

What is claimed is:

1. An X-ray detectable surgical dressing having incorporated therein a filament of elastomeric material containing from 40 to 90 percent by weight, based on the weight of the elastomer, of an X-ray opaque filler material comprising a non-toxic element of atomic weight above 100, said filament incorporating throughout its length a continuous reinforcing thread.

2. X-ray detectable dressing according to claim 1, wherein the reinforcing thread is internal to said filament.

3. X-ray detectable dressing according to claim 2, wherein the elastomeric material is polyvinyl chloride.

4. X-ray detectable dressing according to claim 3, wherein the reinforcing thread is a substantially central continuous textile yarn.

5. X-ray detectable dressing according to claim 4, wherein the X-ray opaque substance is powdered barium sulphate.

6. X-ray detectable dressing according to claim 5, wherein the thickness of the filament is such as to provide an X-ray opaque transverse path through the filament, of at least 28 mils.

* * * * *

UNITED STATES PATENT AND TRADEMARK OFFICE
CERTIFICATE OF CORRECTION

PATENT NO. : 4,185,626

DATED : December 20, 1977

INVENTOR(S) : Graham Jones and Geoffrey Unwin

It is certified that error appears in the above-identified patent and that said Letters Patent are hereby corrected as shown below:

On the cover page, insert the following in the appropriate order in the left-hand column:

— [30] Foreign Application Priority Data
December 20, 1976 [UK] United Kingdom...53114/76 —

Signed and Sealed this

Twenty-ninth Day of September 1981

[SEAL]

Attest:

GERALD J. MOSSINGHOFF

Attesting Officer    Commissioner of Patents and Trademarks